(12) United States Patent
Al-Qaoud et al.

(10) Patent No.: US 10,010,564 B2
(45) Date of Patent: Jul. 3, 2018

(54) CAMEL MILK-BASED TOPICAL PHARMACEUTICAL COMPOSITION

(76) Inventors: Khaled Mahmood Al-Qaoud, Amman (JO); Penelope Agmad Shihab, Amman (JO); Luay Fawzi Abu-Oatousch, Amman (JO); Christopher R. Lowe, Cambridge (GB)

( * ) Notice: Subject to any disclaimer, the term of this patent is extended or adjusted under 35 U.S.C. 154(b) by 245 days.

(21) Appl. No.: 13/609,342

(22) Filed: Sep. 11, 2012

(65) Prior Publication Data

US 2014/0072648 A1  Mar. 13, 2014

(51) Int. Cl.
*A61K 35/20* (2006.01)
(52) U.S. Cl.
CPC .................................. *A61K 35/20* (2013.01)
(58) Field of Classification Search
CPC ..................................................... A61K 35/20
USPC ........................................................ 424/535
See application file for complete search history.

(56) References Cited

U.S. PATENT DOCUMENTS

2007/0154443 A1* 7/2007 Kalejman ..................... 424/74
2011/0268743 A1* 11/2011 Benyacoub et al. ....... 424/157.1

FOREIGN PATENT DOCUMENTS

| CN | 101045750 | * 10/2007 |
| WO | WO 2008/013455 | * 1/2008 |
| WO | WO 2011/104565 | * 9/2011 |

OTHER PUBLICATIONS

Madany, R.M. BioTechnology: An Indian Journal. 2009. vol. 3, No. 1, pp. 30-34.*
Shamsia, S.M. International Journal of Genetics and Molecular Biology. 2009. vol. 1, No. 2, pp. 52-58.*
Hurley et al. Nutrients. 2011. vol. 3, pp. 442-474.*
Dinsmore et al. J. Dairy Sci. 1995 vol. 78, No. 9, pp. 1932-1936.*
Odongo et al. Current Res. Nutr. Food Sci. 2016. vol. 4, No. 2, pp. 80-89.*
Website document entitled "Camel milk and cheese making". First available online in 2002. 8-pages. Obtained from http://www.fao.org.*
Seifu, E. Livestock Research for Rural Development. 2007. vol. 19, No. 6, 8-pages.*
Templemans Plat-Sinnige, Marijan J., et al., Induction of *Staphylococcus aureus*-specific IgA and agglutination potency in milk of cows by mucosal immunication, Vaccine 27 (2009) 4001-4008.
Shimazaki, Yoshihiro, et al., Passive Immunization with Milk Produced from an Immunized Cow Prevent Oral Recolonization by *Streptococcus mutans*, Clinical and Diagnostic Laboratory Immunology, Nov. 2001, p. 1136-1139.
Takahashi, N., et al., Immunoglobins in milk from cows immunized with oral strains of Actinomyces, Prevotella, Porphyromonas, Fusobacterium, J Dent Res. Aug. 1992; 71(8): 1509-15.
Shabo, Yosef, et al., Camel Milk for Food Allergies in Children, Immunology and Allergies, vol. 7, Dec. 2005, 796-798.
Unknown Author, website: www.kamelka.nl/kamelka-bonbons-made-entirely-from-camel-milk/.
Office Action from related United Kingdom Application No. GB 1316112.0, dated Feb. 27, 2014, 3 pgs.
Office Action from related United Kingdom Application No. GB 1316112.0, dated Apr. 12, 2017, 3 pgs.
Office Action from related United Kingdom Application No. GB 1316112.0, dated May 10, 2017, 2 pgs.

* cited by examiner

*Primary Examiner* — Chris R Tate
(74) *Attorney, Agent, or Firm* — The Law Firm of Brett M. Maland

(57) ABSTRACT

The present invention relates to a novel pharmaceutical composition with milk of immunized camelid, particularly *Camelus dromedarius* as the main component (i.e. active ingredient) and a method for the treatment or prevention of skin or mucus membrane infections, particularly *Acne vulgaris*. The present invention also discloses a process of preparing said composition.

13 Claims, 5 Drawing Sheets much CAMEL MILK-BASED TOPICAL
PHARMACEUTICAL COMPOSITION

FIELD OF THE INVENTION

The present invention relates to a pharmaceutical composition for the treatment or prevention of skin or mucus membrane infections such as acne, and more particularly, the invention relates to a pharmaceutical composition based on immunized camelid milk, particularly *Camelus dromedarius* as the active ingredient, and a process of preparing the composition.

BACKGROUND OF THE INVENTION

*Acne vulgaris* caused by the bacterium *Propionibacterium acne* (*P. acne*) is the most common cutaneous disorder with a prevalence of 70-85% in adolescents. Although acne is not a life-threatening disease, it has significant physical and psychological effects such as permanent scarring, poor self-image, social inhibition, depression, anxiety, and suicidal tendency. Therefore, acne may be regarded as a serious medical condition. Topical therapy is inevitable in acne treatment and is mainly indicated in the mild to moderate acne. In more severe forms, a combined topical and systemic therapy is recommended. The available topical agents have a direct or indirect influence on the patho-genetic factors and are selected according to the predominant type of acne lesions. The therapeutic success, in acne and related skin disorders are highly dependent on a regular application of the topical agents over a prolonged period of time. However, disadvantages associated with the commonly used topical agents considerably affect the patient compliance and obstruct the treatment. Currently, available treatment for acne and related skin disorders is mostly based on antibiotics and retinoids. The uses of antibiotics have a lot of limitations due to development of resistance by bacteria. On the other hand, Retinoids are highly teratogenic.

Animal milk has been used in the preparation of pharmaceutical and cosmetic compositions. Milk of ruminants, and predominantly bovine milk, has been utilized most. Among drawbacks of cow milk is a wide-spread allergy to it affecting in several of its forms as much as 50% individuals in some populations. It is an object of this invention to provide a composition comprising immunized milk which keeps all the benign properties of milk but is free of the drawbacks related to cow milk. Camel milk has been traditionally used by certain ethnic groups, and it was found that, in some respects, its composition is closer to the human milk than cow milk.

Passive immunity is provided to newborns by Immunoglobulins present in colostrum until its own immune system matures. The concentration in colostrum of specific antibodies against pathogens can be raised by immunizing a mammal with these pathogens or their antigens. Immunized milk products are preparations made of such hyper-immune colostrum or antibodies enriched from it. These preparations can be used to give effective specific protection against different diseases. Colostral immunoglobulin supplements designed for farm animals are commercially available in many countries. Also some immunized milk products that contain specific antibodies against certain pathogens have been launched in the market. A number of clinical studies are currently in progress to evaluate the efficacy of immunized milks in the prevention and treatment of various human infections, including those caused by antibiotic resistant bacteria. Bovine colostrum-based immunized milk products are used as prophylaxis against various infectious diseases in humans. Immunized milk products are examples of health-promoting functional foods, or nutraceuticals.

SUMMARY OF THE INVENTION

It is an object of the present invention to eliminate the disadvantages of the prior art by providing a pharmaceutical composition comprising treated immunized camelid milk in a pharmaceutically acceptable vehicle for the treatment or prevention of skin or mucus membrane infections.

A second object of the present invention, is to provide a process of preparing the composition comprising;
  a. Immunizing a female camelid with a vaccine of *propionobacterium acne, Staphylococcus aureus, Streptococcus mutans, Pseudomonas aeroginosa, Haemophilus influenza, Neisseriae* spp. *Candida* spps or *Chlamydia trachomatus;*
  b. Obtaining milk from the camelid;
  c. Treating the milk at a temperature of 0° C. for 1-2 hours and centrifuging at 15000 rpm to remove lipids;
  d. Treating the milk with rennin or acetic acid to reduce protein content;
  e. Pasteurizing the milk at a temperature ranging from 65° C. to 72° C. for 15 minutes; and
  f. Preparing the milk in a pharmaceutically acceptable vehicle.

Another object of the present invention is to provide a method for the treatment or prevention of skin or mucus membrane infections, comprising applying to infected areas of the human body an effective amount of the composition of the invention.

Preferably, the camelid described in the invention is chosen from the genus *Camelus, Llama,* or *Vicuna*. More preferably, the camelid is *Camelus dromedaries.*

The camelid described in the invention is immunized with skin or mucus membrane pathogen; preferably *propionobacterium acne, Staphylococcus aureus, Streptococcus mutans, Pseudomonas aeroginosa, Haemophilus influenza, Neisseriae* spp. *Candida* spps or *Chlamydia trachomatus.*

Preferably, the pharmaceutical composition of the invention is in the form of cream, ointment, gel, skin wash, lotion, soap, shampoo, mouth wash, vaginal wash, eye wash, tooth paste, or spray.

DETAILED DESCRIPTION OF THE INVENTION

Figure 1:
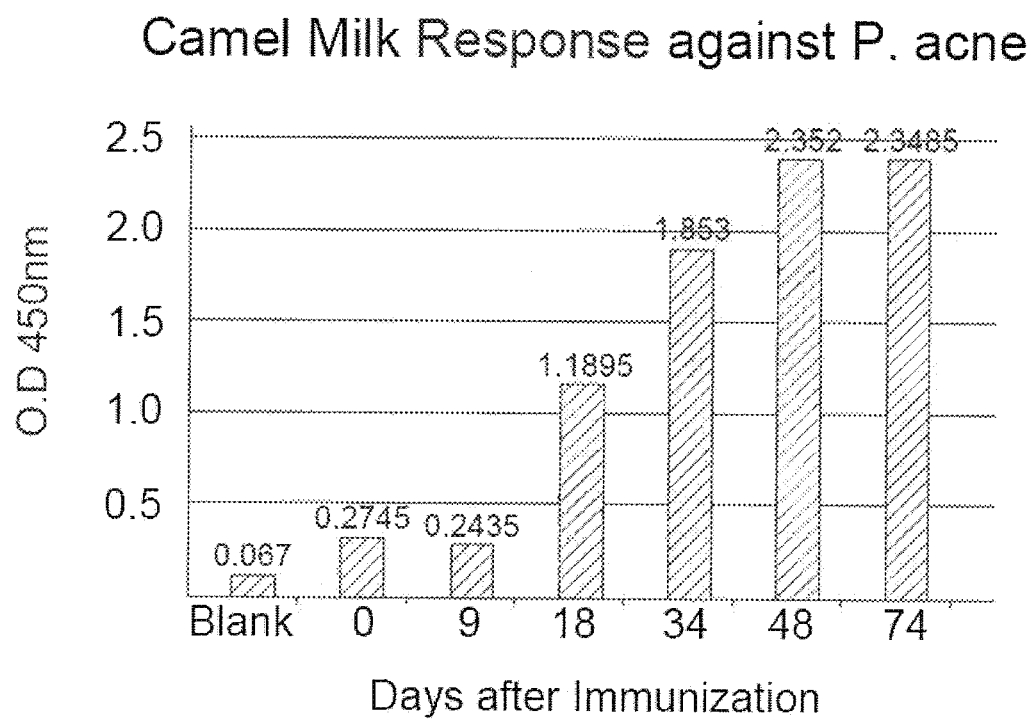
FIG. 1 shows whey of immunized camel tested by Enzyme-Linked Immunosorbent Assay (ELISA) and the kinetic response over the experiment period.

The pharmaceutical composition of this invention comprises immunized camelid milk as the active ingredient in a pharmaceutically acceptable vehicle, in addition, a method for treatment or prevention of skin or mucus membrane infections is described, for example, *acne vulgaris*.

The camelid, preferably Arabian camel (*Camelus dromadarius*) immunized subcutaneously with an initial dose of 3 ml of prepared skin or mucus membrane pathogen, for example, *Propionibacterium acne* vaccine. The vaccinated camel is boosted 4 times at 2 week intervals with 5 ml of vaccine for each booster.

The *Propionibacterium acne* vaccine is prepared from *P. acnes* (NCTC 373), as shown in Examples 1 and 2.

The pharmaceutical composition, according to the present invention, is intended for treating the skin, and may be in a pharmaceutically acceptable vehicle in the form which include, but is not limited to liquid, paste, or solid, and more particularly in the form of ointment, cream, milk, powder, impregnated pad, wipes, solution, gel, spray, suspension, lotion, shampoo, or washing base. The composition may also be in the form of suspension of lipid or polymer vesicle, nano sphere or micro sphere, or polymer patches and hydrogels allowing a controlled release. The composition may be in anhydrous form, in aqueous form, or in the form of an emulsion. The components of the pharmaceutical composition and their ratios could be adjusted according to the pharmaceutically acceptable vehicle and the intended application of the pharmaceutical composition. In a preferred embodiment of the present invention, the pharmaceutical composition is in the form of a cream, and in another preferred embodiment of the present invention, the pharmaceutical composition is in the form of a gel.

The present invention further relates to a process of preparing the pharmaceutical composition, comprising.
1. Immunizing a female camel with a vaccine of intact or whole cell lysate of *P. acne*;
2. Obtaining milk from the female camel;
3. treating the female camel milk at a temperature of 0° C. for 1-2 hours and centrifuging at 15000 rpm to remove lipids;
4. Treating the milk with rennin or acetic acid to reduce protein content;
5. Pasteurizing the camel milk at a temperature ranging from 65° C. to 72° C. for 15 minutes; and
6. Preparing the camel milk in a pharmaceutically acceptable vehicle.

The invention will be further described and illustrated in the following examples.

EXAMPLES

The following examples illustrate the present invention without, however, limiting the same thereto.

Example 1

Cell Culture

*P. acnes* (NCTC 373) were cultured on Mueller Hinton Agar (MHA) under anaerobic conditions using Gas-Pak (Oxoid) at 37° C. for 72 hrs. Standard inoculums of Optical Density 600 (OD600)=1.0-3.0 were prepared by inoculating colonies of *P. acne* in Phosphate Buffered Saline (PBS).

Example 2

Bacteria Harvesting

1. The bacterial cells were harvested by adding 1 ml of autoclaved PBS 1× to the growing bacteria and collected from the plate with a sterile Pasteur pipette;
2. The bacteria were washed 3 time with PBS;
3. The suspension was prepared as 2 McFarland standard/1.5 ml;
4. The bacteria were inactivated by heating at 60° C. for 30 min and centrifuged at 5,000×g for 5 min;
5. The bacteria were mixed with PBS until reaching the required McFarland/1.5 ml; and 1.5 ml of the inactivated bacteria were mixed with 1.5 ml of the Freund's adjuvant complete (SIGMA) and injected subcutaneously into a camel.

Example 3

Camel Immunization

For each infection model, two adult female Arabian camels (*Camelus dromedarius*) were used; one as control and the other was immunized subcutaneously with an initial dose of 3 ml of prepared *Propionibacterium acne* vaccine. The vaccinated camel was boosted 4 times at 2 week intervals with 5 ml of the vaccine for each booster. The two camels were kept in a farm for two months, and were kept under similar conditions.

Example 4

Detection of Specific Antibodies Against *Propionibacterium Acne* in Milk by Enzyme-Linked Immunosorbent Assay (ELISA)

For milk antibody screening, the ELISA, was performed. Flat bottomed 96 well polystyrene micro titer plates (Greiner, Germany) were coated with 100 µl of 10 µg/ml *Propionibacterium acne* antigens in carbonate-bicarbonate buffer (pH 9.6) overnight at 4° C. The plates were washed 3 times with 100 µl of 0.15 M PBS (pH 7.2) containing 0.05% Tween 20 and blocked with 100 µl of 2% Bovine Serum Albumin (BSA) in PBS for one hour at Room Temperature (RT). The plates were washed again and 100 µl of the serum samples diluted at 1:100 in 1% BSA were added in duplicates and incubated for one hour at RT, whereas, milk samples were added in duplicates without dilution. Negative and positive control samples were incorporated in each of the plates. After washing, 100 µl of one of the horse radish peroxidase (HRP) conjugated protein A and protein G were diluted at 1:1000 in 1% BSA, and were added separately to each well. The plates were incubated for one hour at RT and washed again. Finally, 100 µl of 0.1% O-phenylenediamine (Sigma, USA) containing hydrogen peroxide in 0.1 M citrate buffer (pH 4.5) were added to each of the wells and absorbance was measured at 490 nm using ELISA reader (AsysHitech, Switzerland). Results are shown in FIG. 1.

Example 5

Identification of Camel Milk Proteins Using Sodium Dodecyl Sulfate Polyacrylamide Gel Electrophoreses (SDS-PAGE)

Figure 2:
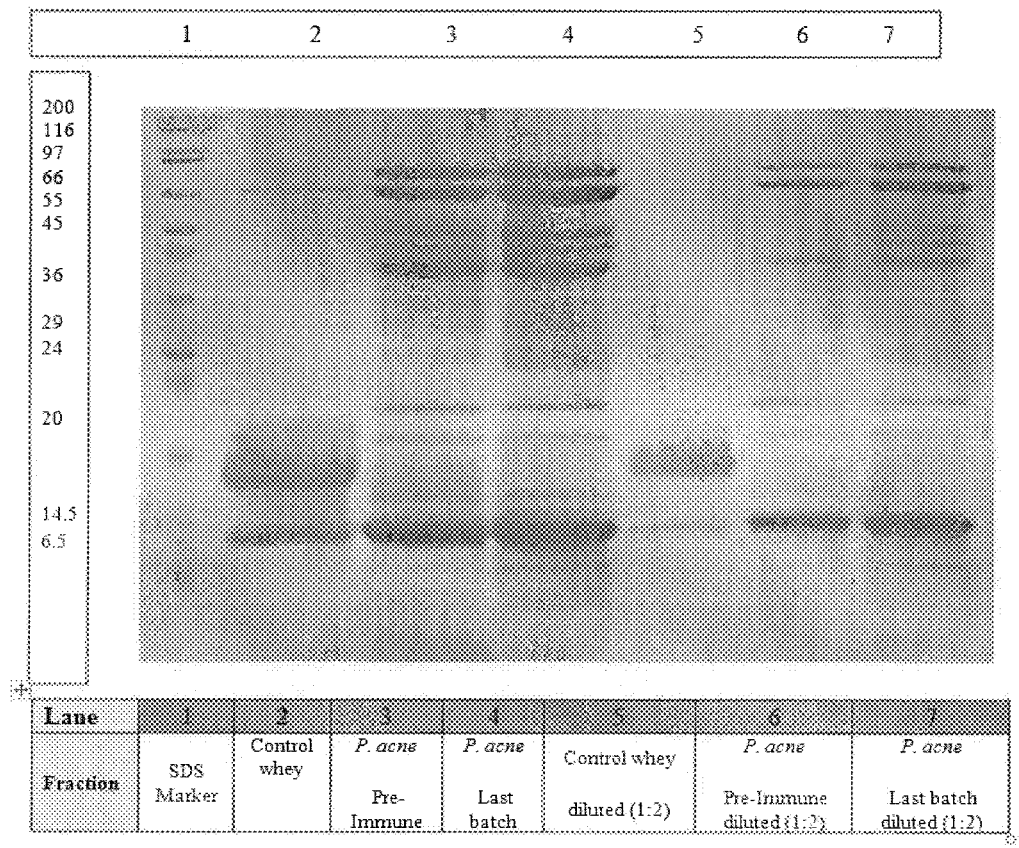
FIG. 2 shows Coomassie SDS-PAGE gel (12.5%) for *P. acne* camel whey. The run was done for 30 min at 100V, then for 45 min at 150V. Load was 20 µl/well. Dilution was (3:1) with 4× dye for all fractions.

Components of camel skimmed milk were fractionated by SDS-PAGE (after precipitation of casein). This was performed using Desaphor VE minigel (Heidelberg, Germany) in the discontinuous buffer system using 0.5 mm thick 10% acrylamide-bisacrylamide gels under non-reducing conditions as described by Hamers-Casterman et al. (1993). For preparing resolving gels, 4 mL distilled water, 2.5 mL running buffer (pH 8.8), 3.3 mL of 30% acrylamide-bisacrylamide solution, 100 μL of 10% ammonium persulfate (APS) and 10 μL Tetramethylethylenediamine (TEMED) were mixed. Stacking gels (4%) were prepared by adding 6 ml of distilled water, 2.5 ml staking buffer (pH 6.6), 1.3 mL of 30% acrylamide-bisacrylamide solution, 100 μl of 10% Ammonium persulfate (APS), and 10 μl TEMED. The milk was mixed with an equal volume of sample buffer lacking B-mercaptoethanol (non-reducing conditions) (pH 6.8). For band size determination, molecular weight protein standard was used after being processed in a similar way as the milk samples. Electrophoresis was carried out using running buffer with pH 8.3 at 120 volts for 60-120 minutes. The gel was stained with Coomassie brilliant blue R-250 (except if used for immunoblot) and destained by 20% acetic acid until clear bands were seen. Results are shown in FIG. 2.

Example 6

In Vitro Activity of Whey Against Acne

Figure 3:
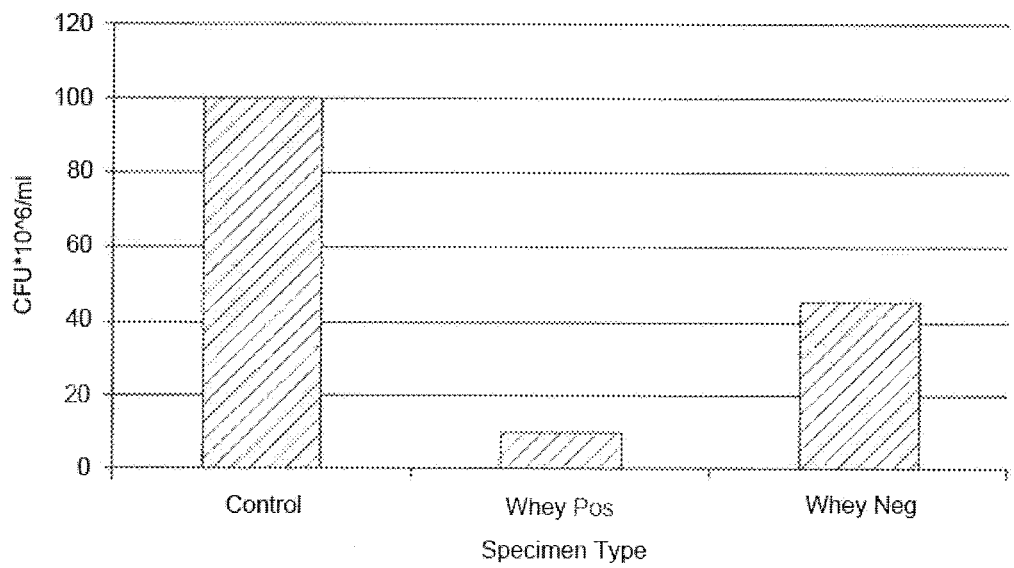
FIG. 3 shows bactericidal activity of whey obtained from milk of immunized camel on *P. acne.*
Figure 4:
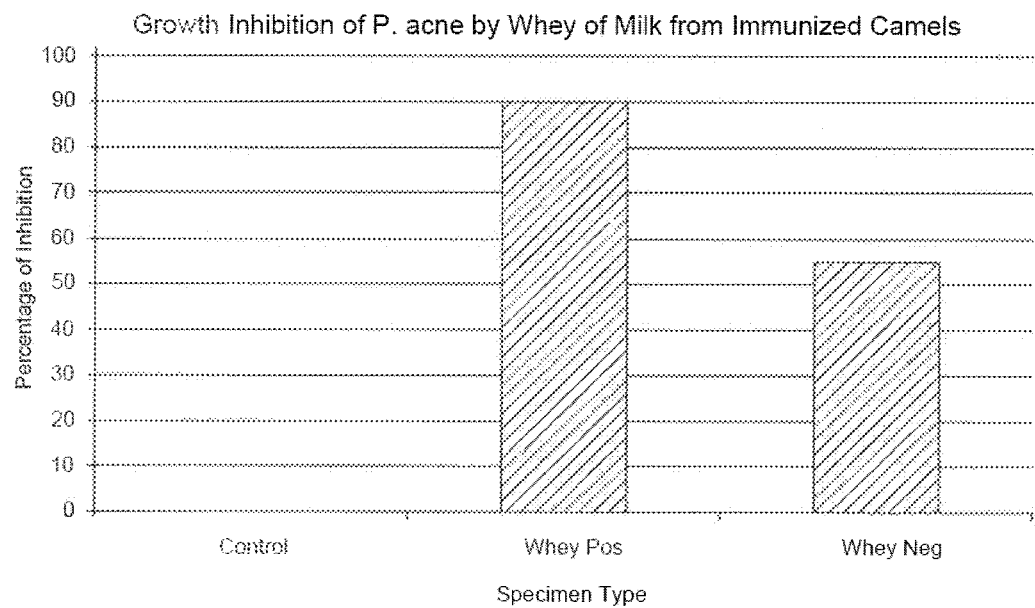
FIG. 4 shows the growth inhibition of whey obtained from milk of immunized camel.

Antibodies isolated from whey of Camel milk immunized with killed *P. acne* are mixed with a standard inoculum of the bacterium and subsequently incubated for 72 hrs. The total count is determined and then compared with the total count of the standard inoculum without mixing with the antibodies. Results are shown in FIG. 3 and FIG. 4.

Example 7

Preparation of Cream Formula

For the treatment of acne, a cream formula has been prepared from the following components:
Cream Formula 0.5% w/w

| Material | weight | mg/unit |
|---|---|---|
| Camel dried whey* | 15 g | 2.5 |
| Cetyl alcohol | 90 g | 15 |
| Tween 20 | 30.9 ml | 5.15 |
| Glycerylmonostearate type1 | 17.1 g | 2.85 |
| MERKUR 791 | 60 g | 10 |
| Purified water | 387 ml | 64.5 |
| Total | 600 | 100 |

*Equivalent to 0.5% w/w total protein

Preparation Protocol:
1. Cetyl alcohol, Glyceryl monostearate and Merkur were molten in same container at 75 C using water bath;
2. Tween 20 was mixed with purified water;
3. Camel whey powder was dissolved in Tween mixture;
4. The mixture from step 3 was heated to 45°-50° C.;
5. The mixtures from step 1 was cooled to 65°-70° C.; and
6. Both mixtures were mixed together and cooled while mixing until cream turns white.

Example 8

Preparation of Gel Formula

For the treatment of acne, a gel formula has been prepared from the following components:
Gel Formula 0.5% w/w

| Material | weight | mg/unit |
|---|---|---|
| Camel dried whey* | 8.75 g | 2.5 |
| Hydroxypropyl cellulose grade HF | 10.5 g | 3 |
| Deionized (D.I.) water | 330.75 ml | 94.5 |
| Total | 350 g | 100 |

*contains 0.5% total protein.

Preparation Protocol:
1. Camel dry whey was dissolved in D.I. water;
2. Hydroxypropyl cellulose grade HF was dissolved in solution from step 1,
3. The mixture was continuously mixed until a clear homogenous gel has formed; and
4. The gel was filled in tubes.

Example 9

Recovery of Active Ingredients from Cream

Figure 5:
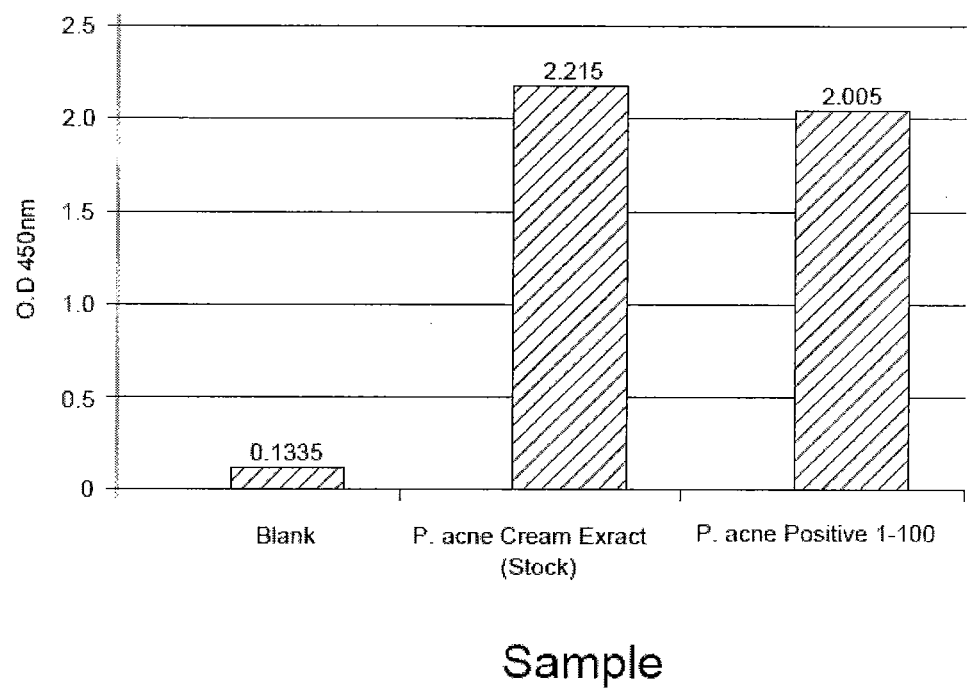
FIG. 5 shows anti-acne activity of aqueous cream extract.

The active ingredients of camel milk whey were re-extracted from the cream for the purpose of stability testing. The cream was mixed with equal volumes of PBS and incubated in water bath at 56° C. for 10 minutes. The mixture was then centrifuged at 13400 rpm for 10 minutes, using microfuge. The aqueous phase was collected and tested using ELISA. Results are shown in FIG. 5.

Example 10

In Vivo Testing of the Efficacy of Whey Protein Concentrate of Milk of Immunized Camel Against *Propionibacterium Acne* Protocol

*Propionibacterium acne* ($10^8$ CFU/ml ($OD_{600}$=2)) bacteria were mixed with the whey protein concentrate and incubated for 2 hrs before Intradermal injection in the central portion of rabbit ear. Both positive whey and negative whey were used and compared. Injection was gradually performed by 28 gauge needle to prevent leakage. Gross examination was performed daily along the period of investigation (two weeks). Histopathological evaluation was performed after sacrificing the animals.
Results:
Gross Examination:
Ear thickness: the infection induced rabbit showed double fold increased ear thickness compared to the normal non infected ear. In contrast, ear thickness was significantly reduced in cases of injecting pretreated bacteria with positive whey and less significantly in cases of negative whey. In addition, no significant differences were observed concerning redness, heat, formation of papules and pus.
Histopathological Examination:
In the infection induced rabbit, the inflammatory response was presented with dense mixed inflammatory cells and marked eosinophilia, formation of micro abscess and ulcerations without affecting the epidermis. In contrast, mild mixed inflammatory cells without ulceration and less micro abscesses were markedly observed in cases of injecting pretreated bacteria with positive whey. No differences were observed in the negative whey treated rabbit in comparison to the infection induced ear.

Microbiological Examination

The recovery of viable *P. acne* was possible in cases of pus formation. No differences were seen among all groups.

While the present invention has been described in details and with reference to specific embodiments thereof, it will be apparent to one skilled in the art that various additions, omissions and modifications can be made without departing from the spirit and scope thereof.

The invention claimed is:

1. A topical pharmaceutical composition for treating or preventing acne comprising an effective amount of immunized Camelid milk, wherein the topical pharmaceutical composition is prepared by the steps of:
    immunizing a Camelid with *Proprionibacterium acnes* by artificially injecting the Camelid with said *Proprionibacterium acnes*,
    obtaining milk from the immunized Camelid;
    treating the obtained milk with rennin or acetic acid under conditions suitable to reduce the protein content of the milk;
    adding a topical pharmaceutically-acceptable vehicle to the treated milk,
    wherein said topical pharmaceutical composition is in a form selected from the group consisting of a cream, an ointment, a gel, a skin wash, a lotion, a soap, a shampoo, and a spray.

2. The pharmaceutical composition of claim 1, wherein said Camelid is from the genus *Camelus, Llama*, or *Vicuna*.

3. The pharmaceutical composition of claim 2, wherein said Camelid is *Camelus dromedarius*.

4. The pharmaceutical composition of claim 1, wherein said *Proprionibacterium acnes* is intact and inactivated with heat.

5. The pharmaceutical composition of claim 1, wherein said exposed milk is further treated at a temperature of 0° C. for 1-2 hours and centrifuged at 15000 rpm for the removal of lipids.

6. A process for preparing a topical pharmaceutical composition for preventing or treating acne, comprising the steps of:
    immunizing a Camelid with *Proprionibacterium acnes* by artificially injecting the Camelid with said *Proprionibacterium acnes*,
    obtaining milk from the immunized Camelid;
    exposing the obtained milk to a temperature of 0° C. for 1-2 hours and centrifuging the milk at 15000 rpm to remove lipids therefrom;
    treating the exposed milk with rennin or acetic acid under conditions suitable to reduce the protein content of the lipid-removed milk;
    pasteurizing the treated milk at a temperature ranging from 65° C. to 72° C. for 15 minutes; and
    adding a topical pharmaceutically-acceptable vehicle to the pasteurized milk.

7. The process of claim 6, wherein said Camelid is from the genus *Camelus, Llama*, or *Vicuna*.

8. The process of claim 7, wherein said Camelid is *Camelus dromedarius*.

9. The process of claim 6, wherein said composition is in the form of a cream, an ointment, a gel, a skin wash, a lotion, a soap, a shampoo, or a spray.

10. A method for preventing or treating acne in a human in need thereof comprising applying an effective amount of the topical pharmaceutical composition of claim 1 to an area of skin of said human.

11. A process for preparing a topical pharmaceutical composition for preventing or treating acne, comprising the steps of:
    immunizing a Camelid with *Proprionibacterium acnes* by artificially injecting the Camelid with said *Proprionibacterium acnes*,
    obtaining milk from the immunized Camelid;
    treating the obtained milk with rennin or acetic acid under conditions suitable to reduce the protein content of the milk;
    adding a topical pharmaceutically-acceptable vehicle to the treated milk,
    wherein said topical pharmaceutical composition is in a form selected from the group consisting of a cream, an ointment, a gel, a skin wash, a lotion, a soap, a shampoo, and a spray.

12. The process of claim 11, wherein said Camelid is from the genus *Camelus, Llama*, or *Vicuna*.

13. The process of claim 12, wherein said Camelid is *Camelus* dromedarius.

* * * * *